United States Patent [19]

Gay et al.

[11] Patent Number: 4,461,918
[45] Date of Patent: Jul. 24, 1984

[54] PROCESS FOR PRODUCING PENTACHLORONITROBENZENE FROM HEXACHLOROBENZENE

[75] Inventors: Walter A. Gay, Cheshire; Robert F. Dietrick, Clinton, both of Conn.

[73] Assignee: Uniroyal, Inc., Middlebury, Conn.

[21] Appl. No.: 461,885

[22] Filed: Jan. 28, 1983

Related U.S. Application Data

[63] Continuation-in-part of Ser. No. 444,757, Nov. 26, 1982.

[51] Int. Cl.$^3$ .............................................. C07C 79/12
[52] U.S. Cl. ...................................... 568/938; 568/67
[58] Field of Search ................................ 568/937, 938

[56] References Cited

U.S. PATENT DOCUMENTS

| | | | |
|---|---|---|---|
| 3,984,487 | 10/1976 | Watts et al. | 568/938 |
| 4,057,590 | 11/1977 | Gay | 568/938 |
| 4,138,438 | 2/1979 | Gay | 568/938 |

*Primary Examiner*—Leland A. Sebastian
*Attorney, Agent, or Firm*—Marvin Bressler

[57] ABSTRACT

Disclosed is a process for producing pentachloronitrobenzene (PCNB) by reacting hexachlorobenzene (HEX) with sodium hydrosulfide (NaSH) in the presence of sodium hydroxide (NaOH), sodium carbonate (Na$_2$CO$_3$), or mixtures thereof to produce the sodium salt of pentachlorothiophenol (PCTP), followed by reacting it (or PCTP itself after acidifying) with nitric acid in the presence of sulfuric acid or oleum.

14 Claims, No Drawings

PROCESS FOR PRODUCING PENTACHLORONITROBENZENE FROM HEXACHLOROBENZENE

CROSS-REFERENCE TO RELATED APPLICATIONS

This application is a continuation-in-part application of U.S. patent application Ser. No. 444,757, filed by the same inventors on Nov. 26, 1982.

BACKGROUND OF THE INVENTION

1. Field of the Invention

This invention relates to the production of pentachloronitrobenzene.

2. Brief Description of the Prior Art

Pentachloronitrobenzene (sometimes referred to herein as PCNB) is widely used today as a soil fungicide. It is particularly useful in controlling plant diseases caused by botrytis, fusarium, rhizoctonia and anthracnose.

Several methods are known for the preparation of PCNB. For example, U.S. Pat. No. 4,026,955, which issued on May 31, 1977 to Breaux, Newman and Quinnett, teaches one such process. That patent teaches reacting pentachlorobenzene and a mixed nitration acid in three stages having specific temperature requirements. U.S. Pat. No. 4,057,590, which issued on Nov. 8, 1977 to Gay, discloses a low temperature process for making PCNB by reacting pentachlorobenzene with substantially pure nitric acid. Also, U.S. Pat. No. 4,138,438, which issued on Feb. 6, 1979 to Gay, teaches another multi-step reaction between pentachlorobenzene and a mixed nitration acid and HCl. And U.S. Pat. No. 4,147,732, which issued on Apr. 3, 1979 to Mendiratta, discloses a process with a two-stage reactant mixing step wherein pentachlorobenzene is first mixed with sulfuric acid and then concentrated nitric acid is added.

While the processes disclosed by these four references represent significant advances in producing relatively high purity PCNB, there is still a need in the art to be able to produce high purity PCNB from precursors other than pentachlorobenzene, which is not always commercially available. The present invention covers such a process for making PCNB through a precursor that was unthought of for this use until the present invention.

BRIEF SUMMARY OF THE INVENTION

The present invention, therefore, is directed to a process for producing pentachloronitrobenzene comprising (1) reacting hexachlorobenzene (HEX) with sodium hydrosulfide (NaSH) in the presence of an inorganic base selected from the group consisting of sodium hydroxide, sodium carbonate and mixtures thereof to produce the sodium salt of pentachlorothiophenol (PCTP); and (2) reacting this sodium salt of pentachlorothiophenol with a mixed nitration acid comprising nitric acid and sulfuric acid (and, preferably, sulfur trioxide to form oleum) at a temperature from about 35° C. to about 110° C. to form pentachloronitrobenzene, the nitric acid being in molar excess of the pentachlorothiophenol.

A preferred embodiment of this invention is directed to acidifying the sodium salt of PCTP with a mineral acid (e.g. HCl) to form PCTP itself, which is reacted with the nitric acid in the manner mentioned in step (2) above to form PCNB. This acidifying step facilitates processing when a solvent is employed in step (1), above, and appears to result in a purer PCNB product.

DETAILED DESCRIPTION

An important advantage of this invention is that it allows the conversion of hexachlorobenzene, an unwanted by-product of conventional PCNB production methods, back to PCNB. Thus, the unwanted and possibly harmful by-product HEX is converted into the useful PCNB.

In the first step of the process of the present invention, hexachlorobenzene is reacted with NaSH in the presence of NaOH or $Na_2CO_3$ or mixtures thereof. This reaction is illustrated in the following reaction equation (A) wherein NaOH is employed as the inorganic base:

$$C_6Cl_6 + NaSH + NaOH \rightarrow C_6Cl_5SNa + NaCl + H_2O \quad (A)$$

The use of the inorganic bases, NaOH or $Na_2CO_3$, reduces the amount of expensive NaSH necessary to carry out the conversion and eliminates the generation of the highly toxic side-product, hydrogen sulfide ($H_2S$).

The molar ratio of NaSH to HEX is preferably in the range of about 0.75:1 to about 1.25:1. More preferably, it is from about 0.9:1 to about 1.1:1. Most preferably, it is about 1:1.

The mole ratio of NaSH to the inorganic base (NaOH, $Na_2CO_3$ or mixtures thereof) is preferably at least about 1:1. More preferably, it is from about 1:1 to about 1.5:1.

This salt-forming reacting is preferably carried out in the presence of an inert organic solvent. Suitable organic solvents include N,N-dimethylacetamide and dimethylformamide. However, the presence of a solvent is not critical to this invention.

Any suitable reaction temperature may be employed for this reaction step. A preferable range is from about 50° C. to about 100° C. The reaction time is dependent upon the temperature used; suitable reaction time would range from about 30 minutes to about 600 minutes. However, the present invention is not limited to particular reaction temperatures or times.

The sodium pentachlorothiophenolate may be reacted directly in a nitrating medium to form PCNB, or, according to a preferred embodiment, may be first acidified with a mineral acid such as HCl to form pentachlorothiophenol. This latter reaction is illustrated in the following reaction equation (B) wherein HCl is employed as the mineral acid.

$$C_6Cl_5SNa + HCL \rightarrow C_6Cl_5SH + NaCl \quad (B)$$

Other mineral acids besides HCl may be used for this step. These acids include sulfuric and phosphoric acids. Generally, the amount of mineral acid added should be sufficient to convert substantially all of this sodium salt to PCTP.

Any reaction conditions normally used in similar acidification reactions may be used herein and the present invention is not to be limited to any specific reaction conditions for this step.

Either sodium pentachlorothiophenolate or pentachlorothiophenol is reacted with nitric acid in the presence of $H_2SO_4$ or oleum to form PCNB. The exact mechanism of this reaction is not known; but it is believed that the PCTP reacts with $HNO_3$ in the presence of oleum by more than one reaction route. Two theorized routes are illustrated below by reaction equations (C) and (D):

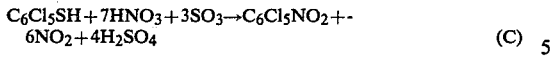  (C)

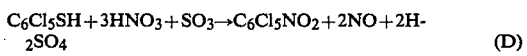  (D)

As can be seen, NO$_2$ or NO is produced as a by-product of each route. Since mixtures of NO$_2$ and NO may be in the resulting reaction mixture, it is believed that the formation of PCNB from PCTP occurs simultaneously by both reaction mechanisms (C) and (D) and possibly others. Of course, the present invention is not to be limited to any particular reaction mechanisms.

The mixed nitration acid reactant for this step is, as indicated above, comprised of sulfuric and nitric acid. It is preferred that sulfur trioxide also be present (as in commercial oleum). While it is not believed to be critical, it is advantageous to employ a weight ratio of sulfuric acid to nitric acid of at least about 0.1:1 in order to achieve desirable yields of PCNB. It is more preferred to employ a weight ratio of at least about 0.2:1, most preferably, from about 0.25:1 to about 1.1:1, of these two acids for optimum yields. Also, it is desirable to employ SO$_3$ in amounts from about 1% to about 30%, more preferably, at least about 10% by weight of the H$_2$SO$_4$ employed.

Sufficient mixed nitration acid should be employed so as to have a molar excess of HNO$_3$ over PCTP. As can be seen from equations (C) and (D), above, the theorized reaction mechanisms require this molar excess. Advantageously, the mole ratio is preferred to be at least about 3:1. More preferably, it is desirable to employ sufficient nitric acid so that the molar ratio is from about 10:1 to about 40:1.

Preferably, the nitric acid and sulfuric acid (oleum may be substituted for the latter) making up this mixed nitration acid are both in the most concentrated form as possible. Desirably, the nitric acid making up part of the mixed nitration acid is concentrated nitric acid having at least about 65%, more preferably at least about 90%, by weight of HNO$_3$. The sulfuric acid is preferably in concentrated form containing at least about 85%, more preferably 95%, by weight of H$_2$SO$_4$.

Sufficient sulfuric acid should preferably be present to act simultaneously as a solvent and catalyst and to absorb water formed during the reaction. In particular, regarding its catalytic effect, it is known that the presence of sulfuric acid protonates the nitric acid and, thus, makes the nitric acid a more reactive species for the present invention. The additional presence of SO$_3$ is preferred because it is believed that a higher yield and a purer product may occur.

The last reaction of the present invention may be conducted by mixing together the PCTP and the mixed nitration acid in one or two stages. For example, one preferred embodiment is to mix the PCTP and concentrated nitric acid in one reaction vessel and then adding concentrated sulfuric acid (or oleum) to this mixture. In another preferred embodiment, the PCTP is added to a mixture of nitric acid and sulfuric acid (or oleum). Alternatively, the acid mixture may be added to the PCTP. However, the mode of addition is not a critical feature of this invention as long as desired reaction temperatures are maintained during the addition period.

The reaction between PCTP and the mixed nitration acid is highly exothermic. In order to control the temperature of the reaction mixture, it is preferred to add the PCTP to the acids, or vice versa, at a rate sufficient to control the temperature to within the desired temperature range. If external cooling is provided more rapid addition may be utilized, but such cooling is not essential. Also, it is preferred that the reaction mixture be well mixed by known stirring or agitation techniques to better ensure proper overall temperature control.

If the above-noted two stage mixing process is employed, the addition of the PCTP to the nitric acid, or vice versa, is preferred to be made at a rate sufficient to maintain the reaction mixture at a temperature from about 35° C. to about 65° C. At temperatures below about 35° C., several production problems may be encountered involving difficult temperature control and inadequate production rates. At an initial reaction temperature above about 65° C., the rate of by-product formations, including the forming of undesired hexachlorobenzene, may occur. Accordingly, it is preferred to conduct this first stage addition within the specified range, more preferably, from about 45° C. to about 60° C. In the second stage, the sulfuric acid or oleum is added to this resulting mixture at a rate sufficient to keep the reaction mixture from about 55° C. to about 100° C. Temperatures below about 55° C. for this stage are not preferred because the reaction rates would be too slow for most commercial modes. Likewise, allowing the reaction temperature to rise above about 100° C. may result in the formation of undesirable impurities like hexachlorobenzene. More preferably, it is desired that this second stage be carried out at temperatures from about 60° C. to about 85° C.

If the above-noted one stage mixing process is employed, the addition of the PCTP to the mixed acids, or vice versa, is preferably carried out from about 55° C. to about 100° C. for the same reasons as stated above. More preferably, the reaction is conducted in a range from about 60° C. to about 85° C. for this single stage.

Regardless of whether one or two-stage mixing steps, or other mixing procedures are followed, the reaction mixture should be maintained at the above-noted temperature range(s) for a sufficient amount of time to convert at least a portion of the PCTP to PCNB. Preferably, the amount of time should be sufficient to convert substantially all (i.e. greater than 95% by weight) of the PCTP. In order to achieve this desired conversion, it is preferred to allow the reaction mixture to react from about 15 minutes to about 180 minutes, or greater. Of course, the reaction time will depend upon the specific reaction temperatures employed and the mole and weight ratios of HNO$_3$:PCTP and HNO$_3$:H$_2$SO$_4$ employed, respectively. To minimize the time period of the reaction, it is preferable to utilize a combination of reaction temperature(s) and mole and weight ratios which results in the substantial complete conversion of PCTP while minimizing the amount of by-products produced.

After the last reaction has achieved its desired completion, the solid PCNB crystals formed may be recovered or subjected to further chemical reaction in the production of other chemicals. Product recovery can be achieved by any suitable technique such as any conventional liquid/solid separation means such as filtration, centrifugation, decanting and the like. Preferably, the temperature of the reaction mixture, after completion of the reaction, is cooled to a temperature from about 0° C. to about 30° C. and then the PCNB is separated from the reaction mixture. The preferred separation means is filtration. This may also be followed by washing with water or any other suitable solvent to remove residuals. Alternatively, a hot filtration without cooling may be preferred in some instances. A highly pure PCNB product may be made according to this invention with the levels of hexachlorobenzene preferably being less than 1.0% by weight of the total PCNB product.

The process of this invention was totally unexpected and surprising because there is no open position on the PCTP molecule for substitution with a nitro group. One would believe that the —SH and —Cl groups would not be readily reactive for substitution. But, if so, a wide variety of co-products would be produced. In the prior art methods of making PCNB, the pentachlorobenzene precursor has one open position on the ring free for substitution with a nitro group. That is not the case here. Furthermore, one might expect that the reaction of the HNO3 with the —SH group on the PCTP compound would form other substituents, such as the "sulfonic acid group."

The following examples further illustrate the present invention. All parts and percentages are by weight unless otherwise expressly indicated.

EXAMPLES 1-4

Preparation of Pentachlorothiophenol

Example 1

Hexachlorobenzene (25.0 g, 0.088 mol) was added to 50 mL of dimethylformamide followed by the addition of 7.4 g (0.096 mol) of 73% sodium hydrosulfide and 7.9 mL (0.079 mol) of 40% aqueous sodium hydroxide. The stirred reaction mixture was heated to 85° C. for 3.0 hr, cooled to room temperature, and poured into 200 mL of water. After 10 min of stirring, the insoluble material was removed by filtration, and the filtrate acidified with 15 mL (0.18 mol) of concentrated aqueous hydrochloric acid. The resulting precipitate was collected by filtration, washed with 100 mL of water, and dried in vacuo giving 22.8 g, 92% of theoretical, of pentachlorothiophenol.

Example 2

The experiment of EXAMPLE 1 was repeated only using 50 mL of N,N-dimethylacetamide instead of 50 mL of dimethylformamide. The resulting product weighed 21.7 g, corresponding to an 88% yield of pentachlorothiophenol.

Example 3

The experiment of EXAMPLE 1 was repeated only using 50 mL of sulfolane instead of 50 mL of dimethylformamide. The resulting product weighed 13.6 g corresponding to a 55% yield of pentachlorothiophenol.

Example 4

The experiment of EXAMPLE 1 was repeated only using sodium carbonate (8.4 g, 0.079 mol) instead of sodium hydroxide. The resulting product weighed 16.9 g corresponding to a 68% yield of pentachlorothiophenol.

Example 5

PCNB from Pentachlorothiophenol Using 70% Nitric Acid and 30% Oleum

Pentachlorothiophenol (10.0 g, 0.035 mol) was added to 60.0 g of 70% nitric acid at room temperature. The reaction mixture was heated at reflux 7 hr followed by stirring at room temperature 16 hr. At this point, 40 mL of 30% oleum (30% by weight sulfur trioxide in sulfuric acid) was added at such a rate that the temperature was maintained between 55° and 60° C. After the addition was complete (30 min), the reaction mixture was heated at 108° C. for 30 minutes. The reaction mixture was then cooled to room temperature, filtered, the product washed with water and dried in vacuo to give 7.6 g (74% yield) of 99.0% PCNB with 1.0% hexachlorobenzene (GC assay).

Example 6A

PCNB from Pentachlorothiophenol Using 99% Nitric Acid and 30% Oleum in a One-pot, Two-step Process Pentachlorothiophenol (10.0 g, 0.035 mol) was added to 60.0 g of 99% nitric acid over 20 min at 45°–50° C. followed by heating at reflux (55° C.) for 1.5 hr. At this point 20 mL of 30% by weight oleum was added at such a rate that the temperature was kept at 75° to 80° C. After the addition was complete (approximately 30 min.), the reaction mixture was cooled to room temperature. The product was collected by filtration, and thoroughly washed with water to give after drying in vacuo, 8.6 g (85% yield) of 99.7% PCNB with 0.17% hexachlorobenzene (GC assay). Variations on this one-pot, two-step process were examined and are summarized in TABLE I.

TABLE I

| | | | ONE-POT, TWO-STEP PCTP TO PCNB PROCESS[a] | | | | | |
|---|---|---|---|---|---|---|---|---|
| EXAMPLE | PCTP (g) | 99% HNO3 (g) | PCTP ADD'N TIME (min)/TEMP (°C.) | REFLUX TIME (min) | 30% OLEUM mL (g) | YIELD (%) | PRODUCT ASSAY (%)[b] PCNB | HEX |
| 6B | 10 | 75 | 30 min(50–60° C.) | 30 | 10(18.8) | 82 | 99.6[c] | 0.08 |
| 6C | 10 | 45 | 30 min(50–60° C.) | 30 | 10(18.8) | 84 | 99.3 | 0.2 |
| 6D | 10 | 30 | 30 min(50–60° C.) | 30 | 10(18.8) | 19 | 99.1 | 0.2 |
| 6A | 10 | 60 | 20 min(45–50° C.) | 90 | 20(37.6) | 85 | 99.7 | 0.17 |
| 6E | 25 | 150 | 40 min(50–60° C.) | 30 | 30(56.6) | 81 | >99.5 | <0.2 |
| 6F | 25 | 150 | 40 min(50–60° C.) | 30 | 25(47.0) | 82 | 99.6 | 0.07 |
| 6G | 25 | 150 | 40 min(50–60° C.) | 30 | 15(28.2) | 53 | >99.5 | <0.2 |
| 6H | 25 | 150 | 40 min(50–60° C.) | 30 | 10(18.8) | 10 | >99.5 | <0.2 |

[a]Procedure and work-up outlined in Example 6A
[b]Measured by GC internal area normalization assay.
[c]Elemental analysis. Calc'd for $C_6Cl_5NO_2$: C, 24.40; Cl, 60.02; N, 4.74. Found: C, 24.18; Cl, 59.68; N, 4.84.

Example 7A

PCNB from Pentachlorothiophenol Using 99% Nitric Acid and 30% Oleum in a One-pot, One-step Process A 10 mL aliquot of 30% oleum was added to 60.0 g 99% nitric acid resulting in a temperature rise to 65° C. Pentachlorothiophenol (10.0 g, 0.035 mol) was added at such a rate that the temperature was maintained between 65° C. and 70° C., with a total addition time of 1.0 hr. The reaction mixture was cooled to room temperature, and the product collected by filtration, followed by a thorough water wash and drying in vacuo. The product, 8.5 g (82% yield), analyzed (GC) as 98.6% PCNB with 0.09% hexachlorobenzene. Variations on this one-pot, one-step process are summarized in TABLE II.

TABLE II

ONE-POT, ONE STEP PCTP TO PCNB PROCESS[a]

| EXAMPLE | PCTP (g) | HNO₃ (g) | 30% OLEUM mL (g) | PCTP ADD'N TIME (min) | Yield (%) | PRODUCT ASSAY (%)[b] | |
|---------|----------|----------|------------------|----------------------|-----------|---------------------|---|
|         |          |          |                  |                      |           | PCNB | HEX |
| 7A | 10 | 60 | 10(18.8) | 60 | 82 | 98.6 | 0.09 |
| 7B | 25 | 113 | 25(47) | 80 | 83 | 97.5 | 0.10 |
| 7C | 25 | 75 | 25(47) | 80 | 74 | 97.3 | 0.09 |
| 7D | 25 | 75 | 25(47) | 80[c] | 72 | not determined | not determined |

[a]Procedure and work-up outlined in Example 7A.
[b]Measured by GC internal area normalization assay.
[c]The addition of PCTP was followed by a 60 min heating step at 70° C.

Example 8

PCNB from Pentachlorothiophenol Using 99% Nitric Acid and Concentrated Sulfuric Acid Pentachlorothiophenol (10.0 g, 0.035 mol) was added to 60.0 g 99% nitric acid over 0.5 hr followed by a 0.5 hr reflux at 55° C. At this point, 10 mL of concentrated sulfuric acid was added over a 10 min period, and the reaction mixture heated at 65°–70° C. for 15 min. The reaction mixture was cooled to room temperature, the product collected by filtration, and thoroughly washed with water giving after drying in vacuo 6.5 g (62% yield) of 98.6% PCNB with 0.54% hexachlorobenzene (GC assay).

Example 9

PCNB from Sodium Pentachlorothiophenolate

The sodium salt of pentachlorothiophenol was prepared by heating at 80° C. for 3 hr a reaction mixture consisting of 25.0 g (0.088 mol) hexachlorobenzene and 15 g (0.195 mol) sodium hydrosulfide (73% assay) in 100 mL DMF. The solvent was removed by distillaton in vacuo and the resulting residue (36.3 g) added to a solution of 45 g of 30% oleum in 150 g of 99% nitric acid which was preheated to 65° C. The addition was made in 0.5 hr while the reaction temperature was maintained at 60°–65° C. by ice-bath cooling. The reaction mixture was cooled to room temperature, filtered, and the residue washed with water. After drying in vacuo 21.3 g of product was obtained which assayed (GC) at 97% PCNB, 0.26% hexachlorobenzene.

What is claimed is:

1. A process for producing pentachloronitrobenzene comprising:
   (a) reacting hexachlorobenzene with sodium hydrosulfide in the presence of an inorganic base selected from the group consisting of sodium hydroxide, sodium carbonate, and mixtures thereof, to form sodium pentachlorothiophenolate; and
   (b) reacting said sodium pentachlorothiophenolate with a mixed nitration acid comprising nitric and sulfuric acid at a temperature from about 35° C. to 110° C. to form pentachloronitrobenzene, said nitric acid being in molar excess of said pentachlorothiophenol.

2. The process of claim 1 wherein said mixed nitration acid further comprises sulfur trioxide.

3. The process of claim 1 wherein the molar ratio of said sodium hydrosulfide to hexachlorobenzene is from about 0.75:1 to about 1.25:1.

4. The process of claim 1 wherein said molar ratio of sodium hydrosulfide to inorganic base is at least about 1:1.

5. A process for producing pentachloronitrobenzene comprising:
   (a) reacting hexachlorobenzene with sodium hydrosulfide in the presence of an inorganic base selected from the group consisting of sodium hydroxide, sodium carbonate, and mixtures thereof, to form sodium pentachlorothiophenolate;
   (b) acidifying said sodium pentachlorothiophenolate with a mineral acid to form pentachlorothiophenol;
   (c) mixing said pentachlorothiophenol with nitric acid at a temperature from about 35° C. to about 65° C., said nitric acid being in molar excess of said pentachlorothiophenol;
   (d) mixing the resulting mixture with sulfuric acid at a temperature from about 55° C. to about 100° C., the weight ratio of said sulfuric acid to said nitric acid being at least 0.1:1, and
   (e) maintaining said reaction mixture within said temperature range for sufficient time to convert at least a portion of said pentachlorothiophenol to pentachloronitrobenzene.

6. The process of claim 5 wherein said mineral acid in step (b) is HCl.

7. The process of claim 6 wherein the molar ratio of said sodium hydrosulfide to hexachlorobenzene is from about 0.75:1 to about 1.25:1.

8. The process of claim 7 wherein the molar ratio of said sodium hydrosulfide to inorganic base is at least about 1:1.

9. The process of claim 8 wherein said mixed nitration acid further comprises sulfur trioxide.

10. A process for producing pentachloronitrobenzene comprising:
    (a) reacting hexachlorobenzene with sodium hydrosulfide in the presence of an inorganic base selected from the group consisting of sodium hydroxide, sodium carbonate, and mixture thereof, to form sodium pentachlorothiophenolate;
    (b) acidifying said sodium pentachlorothiophenolate with a mineral acid to form pentachlorothiophenol;
    (c) mixing said pentachlorothiophenol with a mixed nitration acid comprising sulfuric acid and nitric acid at a temperature from about 55° C. to about 100° C., said nitric acid being in molar excess of said pentachlorothiophenol and the weight ratio of said sulfuric acid to said nitric acid being at least 0.1:1; and maintaining said reaction mixture within said temperature range for sufficient time to convert at least a portion of said pentachlorothiophenol to pentachloronitrobenzene.

11. The process of claim 10 wherein said mineral acid is HCl.

12. The process of claim 11 wherein the molar ratio of said sodium hydrosulfide to said hexachlorobenzene is from about 0.75:1 to about 1.25:1.

13. The process of claim 12 wherein the molar ratio of said sodium hydrosulfide to said inorganic base is at least about 1:1.

14. The process of claim 13 wherein said mixed nitration acid further comprises sulfur trioxide.

* * * * *